United States Patent [19]

Blattner

[11] 3,996,373

[45] Dec. 7, 1976

[54] 2,3-DIHYDRO-1H-DIBENZ[e,g]ISOINDOLE COMPOUNDS

[75] Inventor: Hans Blattner, Riehen, Switzerland

[73] Assignee: Ciba-Geigy Corporation, Ardsley, N.Y.

[22] Filed: Mar. 27, 1975

[21] Appl. No.: 562,602

[30] Foreign Application Priority Data

Apr. 5, 1974   Switzerland .................. 4846/74

[52] U.S. Cl. .......................... 424/274; 260/326.1
[51] Int. Cl.² ............... C07D 209/44; A61K 31/40
[58] Field of Search ............. 260/326.1; 424/274

[56] References Cited

UNITED STATES PATENTS 3,883,553   5/1975   Berezin et al. ............... 260/326.1

OTHER PUBLICATIONS

Shields et al., "Chem. Abstracts," vol. 71, p. 365, No. 81083v, (1969).
Hauptmann, "Chem. Abstracts," vol. 55, p. 4451e, (1961).

*Primary Examiner*—Lewis Gotts
*Assistant Examiner*—S. P. Williams
*Attorney, Agent, or Firm*—Joseph G. Kolodny; John J. Maitner; Theodore O. Groeger

[57] ABSTRACT

2,3-Dihydro-1H-dibenz[e,g]isoindoles substituted in the 2-position by a lower alkyl or a lower alkenyl, or a lower haloalkyl, or a free or an esterified or etherified lower hydroxyalkyl, or a lower oxoalkyl, or a free or an esterified lower carboxyalkyl group, and therapeutically usable salts thereof, such compounds having an antagonistic action against reserpine as well as against tetrabenazine such pharmacological properties characterizing these new compounds as antidepressants.

19 Claims, No Drawings

2,3-DIHYDRO-1H-DIBENZ[e,g]ISOINDOLE COMPOUNDS

The invention relates to new pyrrol derivatives of the general formula I

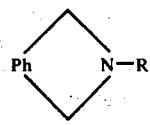

wherein
Ph represents an optionally substituted 9,10-phenanthrylene radical, and
R represents a lower alkyl group, lower alkenyl group or lower haloalkyl group, a free, esterified or etherified lower hydroxyalkyl group, a lower oxoalkyl group or a free or esterified lower carboxyalkyl group,
as well as to the salts thereof, to processes for the production of the new compounds, to pharmaceutical preparations containing these, and to the use of the new compounds as pharmaceutical active substances.

In the compounds of the general formula I, an optionally substituted 9,10-phenanthrylene radical is, for example, a mono- or polysubstituted radical, e.g. a disubstituted radical. If the phenanthrylene radical is substituted, then a mono- or disubstituted radical is preferred, particularly a monosubstituted 9,10-phenanthrylene radical.

Substituents in the 9,10-phenanthrylene radical can be, e.g., halogen, lower alkyl, lower alkoxy, trifluoromethyl or nitro groups. As halogen, these substituents are preferably fluorine, chlorine or bromine.

The radical R can be a lower hydroxyalkyl group etherified with an alcohol, e.g. an alkoxy-lower-alkyl group, especially a lower-alkoxy-lower-alkyl group, or a monoarylmethoxy-lower-alkyl group or diarylmethoxy-lower-alkyl group, e.g. a benzyloxy-lower-alkyl group or diphenylmethoxy-lower-alkyl group. The lower hydroxyalkyl group can be etherified also with a heterocyclic alcohol, e.g. with a 2-oxacycloalkanol, such as tetrahydropyran-2-ol. In addition, the radical R can be a lower hydroxyalkyl group esterified with a carboxylic acid. Examples of such carboxylic acids are arylcarboxylic acids such as benzoic acid, arylalkylcarboxylic acids such as phenylacetic acid, or alkanoic acids, and particularly lower alkanoic acids such as formic acid, acetic acid or propionic acid.

Furthermore, the radical R can be a lower carboxyalkyl group esterified with an alkanol or arylalkanol, or with an alicyclic or heterocyclic alcohol. As alkanols there may be mentioned preferably lower alkanols, such as methanol, ethanol or propanol; as arylalkanols, e.g., benzyl alcohol or phenethyl alcohol; as alicyclic alcohols, e.g., cyclopropylmethanol, cyclopentanol, cyclohexanol, cyclopentylmethanol or cyclohexylmethanol; and as heterocyclic alcohols, e.g., furfuryl alcohol or tetrahydrofurfuryl alcohol, or 2-thiophenemethanol or tetrahydro-2-thiophenemethanol.

Substituents in the 9,10-phenanthrylene radical and the radical R contain as alkyl groups preferably up to 8, especially 1 to 6, carbon atoms. These alkyl groups, which can be straight-chain or branched-chain, are, e.g., the methyl, ethyl, propyl, isopropyl, butyl, isobutyl, pentyl, isopentyl, hexyl, isohexyl, heptyl or octyl group.

As lower alkoxy groups, substituents in the 9,10-phenanthrylene radical can contain, e.g., 1 to 6, especially 1 to 2, carbon atoms. The alkoxy groups, which can be straight-chain or branched-chain, are, for example, the methoxy, ethoxy, propoxy, isopropoxy, butoxy, isobutoxy, pentyloxy, isopentyloxy or hexyloxy group.

As lower alkenyl group, the radical R contains preferably 3 to 4 carbon atoms, particularly 3 carbon atoms. This alkenyl group is present, e.g., as the allyl or 2-methylallyl group.

As lower haloalkyl group, the radical R contains 2 to 5 carbon atoms. This lower haloalkyl group, which can be straight-chain or branched-chain, is, for example, the 2-chloroethyl, 2- or 3-chloropropyl, 2-methyl, 3-chloropropyl, 3-chlorobutyl or 2,2-dimethyl-3-chloropropyl group. Also suitable are corresponding groups containing, instead of chlorine, bromine or fluorine.

As lower oxoalkyl group, the radical R can contain, e.g., 2 to 8, especially 2 to 6, carbon atoms. This oxoalkyl group can be, e.g., the 2-oxoethyl, 2- and 3-oxopropyl, 3-oxobutyl, 3-oxo-4-methyl-pentyl or 3-oxo-4,4-dimethyl-pentyl group.

As lower hydroxyalkyl group, the radical R contains 2 to 8, preferably 2 to 6, carbon atoms. The hydroxyalkyl group, which can be straight-chain or branched-chain, can be, e.g., the 2-hydroxy-ethyl, 1-methyl-2-hydroxy-ethyl, 2- or 3-hydroxy-propyl, 1- or 2-methyl-2-hydroxy-propyl-, 1- or 2-methyl-3-hydroxy-propyl, 2-, 3- or 4-hydroxy-butyl, 3-hydroxy-4-methyl-pentyl or 3-hydroxy-4,4-dimethyl-pentyl group.

As lower-alkoxy-lower-alkyl group, the radical R contains, e.g., 3 to 10, preferably 3 to 6 carbon atoms. This alkoxyalkyl group can be, e.g., the 2-methoxy- or 2-ethoxy-ethyl, 2- or 3-methoxy-propyl, 2- or 3-ethoxy-propyl, 2- or 3-propoxy-propyl, 2- or 3- or 4-methoxy-butyl, 2-, 3- or 4-ethoxy-butyl, 2-, 3- or 4-propoxy-butyl, 2-, 3- or 4-butoxy-butyl, 3-methoxy-4,4-dimethyl-pentyl or 3-propoxy-4,4-dimethyl-pentyl group.

As lower-alkanoyloxy-lower-alkyl group, the radical R contains, e.g., 3 to 10, preferably 3 to 7, carbon atoms. This radical can be, e.g., the 2-formyloxy-ethyl, 2-acetoxy-ethyl, 2-propionyloxy-ethyl, 2- or 3-acetoxy-propyl, 2-methyl-3-acetoxy-propyl, 2- or 3-propionyloxy-propyl, 2-, 3- or 4-acetoxy-butyl, 2-, 3- or 4-propionyloxy-butyl or 3-propionyloxy-4,4-dimethyl-propyl group.

As lower carboxyalkyl group, the radical R contains, e.g., 2 to 8, preferably 2 to 6, carbon atoms. The lower carboxyalkyl group can be, e.g., the carboxy-methyl, 2-carboxyethyl, 2-methyl-2-carboxyl-ethyl, 3-carboxypropyl, 1- or 2-methyl-3-carboxypropyl, 5-carboxypentyl or 7-carboxy-heptyl group.

As lower alkoxycarbonylalkyl group, the radical R contains, e.g., 3 to 8, preferably 3 to 6, carbon atoms. Such alkoxycarbonylalkyl groups are, e.g., the methoxy-, ethoxy- or propoxy-carbonylmethyl, 2-methoxy-, 2-ethoxy- or 2-propoxy-carbonylethyl, 2- or 3-methoxycarbonylpropyl, 2- or 3-ethoxycarbonylpropyl, 2- or 3-propoxy-carbonylpropyl, 2-, 3- or 4-methoxycarbonylbutyl, 2-, 3- or 4-ethoxycarbonylbutyl or 3-methoxycarbonyl-, 3-ethoxycarbonyl- or 3-propoxycarbonyl-4,4-dimethyl-butyl group.

The new compounds possess valuable pharmacological properties. They have an antagonistic action against reserpine, which can be shown in the palpebral fissure test on the rat with intraperitoneal or oral administration in doses of 3–10 mg/kg. In addition, the compounds have, on the same test animal, an antagonistic action against tetrabenazine, as can be shown with intraperitoneal administration of doses of 10–40 mg/kg. besides having these properties, the new compounds exhibit, when administered intraperitoneally in doses of 10 mg/kg and more to the mouse, a central depressant action, which can be ascertained in the orientation motility test on the mouse. The mentioned pharmacological properties characterise the new compounds as antidepressants.

Furthermore, the new pyrrol compounds can be used as starting materials or intermediates for the production of other compounds, particularly therapeutically effective compounds.

Pyrrol compounds of formula I to be emphasised are those wherein Ph represents an unsubstituted 9,10-phenanthrylene radical, and R represents a lower alkyl, lower alkenyl or lower haloalkyl group, a free esterified or etherified lower hydroxyalkyl group, a lower oxoalkyl group or a free or esterified lower carboxyalkyl group, as well as salts of such compounds. Also to be emphasised are pyrrol compounds of formula I wherein Ph represents an unsubstituted 9,10-phenanthrylene radical, and R represents a lower alkyl, lower alkenyl, lower haloalkyl, lower hydroxyalkyl, lower-alkoxy-lower-alkyl, lower-alkanoyl-oxy-lower-alkyl, lower oxoalkyl, lower carboxyalkyl or lower-alkoxycarbonyl-lower-alkyl group, as well as salts of such compounds. Pyrrol compounds of formula I to be particularly emphasised are those wherein Ph reprsents an unsubstituted 9,10-phenanthrylene radical, and R represents a lower alkyl group having 1 to 6 carbon atoms, the allyl group, a lower hydroxyalkyl group having 2 to 6 carbon atoms, or a lower-alkoxy-lower-alkyl group having 3 to 5 carbon atoms, as well as salts of such compounds.

To be more especially emphasised are the following pyrrol compounds embraced by formula I:
2-methyl-2,3-dihydro-1H-dibenz[e,g]isoindole,
2-ethyl-2,3-dihydro-1H-dibenz[e,g]isoindole,
2-isopropyl-2,3-dihydro-1H-dibenz[e,g]isoindole,
2-allyl-2,3-dihydro-1H-dibenz[e,g]isoindole,
2,3-dihydro-1H-dibenz[e,g]isoindole-2-ethanol,
2,3-dihydro-1H-dibenz[e,g]isoindole-2-propanol,
2-(2-methoxyethyl)-2,3-dihydro-1H-dibenz[e,g]isoindole,
as well as the salts of these compounds. Of the mentioned compounds, the one to be emphasised most of all, however, is 2-ethyl-2,3-dihydro-1H-dibenz[e,g]isoindole. In the palpebral fissure test on the rat, this compound is effective administered intraperitoneally in a dosage amount of 3 mg/kg.

The compounds of formula I are obtained by methods known per se. For example, a reactive diester of a diol of the general formula II

is condensed with a compound of the general formula III

wherein Ph and R have the meanings given under formula I.

As reactive diesters of a diol of the general formula II, it is possible to use esters of strong inorganic acids such as, e.g., the bis-hydrochloric acid ester, bis-hydriodic acid ester or, in particular, bis-hydrobromic acid ester or hydrobromic acid/hydrochloric acid ester of such compounds. Also esters of organic acids can be used, e.g. the sulphonic acid esters, such as methanesulphonic acid ester, benzenesulphonic acid ester, p-chloro- or p-bromobenzenesulphonic acid ester or p-toluenesulphonic acid ester. These esters of compounds of the general formula II are condensed preferably in a suitable inert solvent at a reaction temperature of 20° to 130° C. Suitable inert solvents are, for example, hydrocarbons such as benzene or toluene, halogenated hydrocarbons such as chloroform, lower alcohols such as ethanol and particularly methanol, ethereal liquids such as ether or dioxane, as well as lower alkanols, e.g. acetone, methyl ethyl ketone or diethyl ketone, or mixtures of such solvents, e.g. benzene/methanol.

In the reaction according to the invention of one molar equivalent of a diester of a diol of the general formula II with one molar equivalent of a free base of the general formula III there are split off two molar equivalents of acid, which are preferably bound to an acid-binding agent. Suitable acid-binding agents are, e.g., alkali carbonates such as potassium carbonate, or, e.g., alkali hydroxides such as sodium hydroxide or potassium hydroxide, also tertiary organic bases such as pyridine or N-ethyl-diisopropylamine and, in particular, excess base of the general formula III.

Starting materials of formula II are known, e.g. 9-chloromethyl-10-bromomethyl- and 9,10-bis-bromomethyl-phenanthrene [see S. Hauptmann, Chem. Ser. 93, 2604 (1960)]. Further starting materials of this type can be produced in an analogous manner.

In addition, compounds of formula I can be produced, e.g., by a process in which compounds of the general formula IV

wherein Ph has the meaning given under formula I, are alkylated with reactive esters of alcohols of the general formula V

wherein R has the meaning given under formula I, or are alkylated under reducing conditions with aldehydes or ketones which correspond to the alcohols of formula V.

Alkylation of compounds of the general formula IV with reactive esters of compounds of the general formula V is preferably performed in a solvent, in the presence of an acid-binding agent, at a reaction temperature of 20° to 130° C, especially at the boiling temperature of the solvent.

It is possible to use as reactive esters, e.g., halides such as chlorides or bromides, also sulphonic acid esters such as the o- or p-toluenesulphonic acid methyl ester or p-toluenesulphonic acid ethyl ester, or sulphuric acid esters such as, e.g., dimethyl sulphate or diethyl sulphate. Suitable acid-binding agents are alkali metal carbonates such as, e.g., potassium carbonate, or alkali hydroxides such as, e.g., sodium hydroxide, or tertiary organic bases such as, e.g., pyridine or N-ethyl-diisopropylamine. Suitable solvents are ones that are inert under the reaction conditions, for example hydrocarbons such as benzene or toluene, also alkanols such as, e.g., methanol or ethanol, or alkanones such as acetone or methyl ethyl ketone.

Among the starting materials of the general formula IV, 2,3-dihydro-1H-dibenz[e,g]isoindole is known [see E. Mosettig and E. L. May, J. Am. Chem. Soc. 60, 2962–2966 (1963)]. Further starting materials of this type can be produced analogously.

Aldehydes and ketones, which correspond to the alcohols of formula V, are, e.g., lower aliphatic aldehydes or ketones, lower free, esterified or etherified hydroxyoxoalkanes or esterified oxoalkanecarboxylic acids. The reaction product obtained on reaction of these aldehydes or ketones with compounds of formula IV can be reduced in the same operation or subsequently.

The aldehydes, e.g. formaldehyde or acetaldehyde, or the ketones, e.g. acetone, are, for example, heated with the compounds of formula IV in an inert solvent at about 30° to 100° C, and the reaction mixture is subsequently hydrogenated with hydrogen in the presence of a catalyst. Suitable solvents are, e.g., alkanols such as methanol or ethanol; and suitable catalysts are noble metal catalysts such as palladium or charcoal, or alloys of base metals such as Raney nickel.

For reductive alkylation, it is possible to use, instead of hydrogen in the presence of a catalyst, also other reducing agents, e.g. formic acid. In the case of this variant of the process, the stated compounds of the general formula IV are heated with formic acid and the mentioned types of aldehydes or ketones preferably without solvent.

Compounds of formula I can also be produced by reaction of a compound of the general formula IV, wherein Ph has the meaning given under formula I, with a lower epoxyalkane, or with an ester of an $\alpha,\beta$-unsaturated, lower aliphatic carboxylic acid. This reaction is preferably performed in an inert solvent at a temperature of 20° to 100° C. Suitable inert solvents are, for example, hydrocarbons such as benzene or toluene, alkenols such as methanol or ethanol, or ethereal liquids such as dibutyl ether or dioxane.

Subsequent to the reactions according to the invention, there are optionally performed a series of transformations which convert compounds of formula I into other compounds of formula I.

A resultant product of the general formula I of which the radical R represents a lower alkenyl group is optionally hydrated to a product of which the radical R represents a lower hydroxyalkyl group.

The addition of water is effected preferably in the presence of an acid, for example by means of 80% sulphuric acid, and advantageously at a temperature of between 0° and 20° C.

Furthermore, a resultant product of the general formula I of which the radical R represents a lower haloalkyl compound is optionally reacted to a product of which the radical R represents an etherified lower hydroxyalkyl group.

The halogen in this radical R can be, e.g., chlorine, iodine or bromine. This halide is reacted with an alcohol, preferably in a solvent, in the presence of a basic condensation agent, advantageously at a temperature of between 20° and 130° C, preferably at the boiling temperature of the reaction mixture. Suitable condensation agents are, e.g., alkali metal alkanolates such as sodium methylate, or corresponding amides such as sodium amide, or metal hydrides such as sodium or lithium hydride. As solvents it is possible to use, e.g. hydrocarbons such as benzene or toluene, or ethereal liquids such as dioxane; or, if the employed condensation agents are alkali metal alkanolates, the corresponding alkanols can be advantageously be used as solvents.

In addition, a resultant product of the general formula I of which the radical R denotes a lower hydroxyalkyl group is optionally acylated to a product of which the radical R represents an esterified lower hydroxyalkyl group.

Acylation can be performed, e.g., with a carboxylic acid anhydride, or with a corresponding carbonyl halide, at a reaction temperature of between about 20° and 100° C. Since condensation proceeds with the splitting-off of acid, it is advantageous to add to the reaction mixture an acid-binding agent, e.g. a tertiary organic base such as pyridine. An excess of tertiary organic base can also be used as solvent. As solvent, it is also possible to use hydrocarbons, e.g. benzene or toluene, or halogenated hydrocarbons, e.g. chloroform.

A further example is where optionally a resultant product of the general formula I of which the radical R denotes a free lower hydroxyalkyl group is etherified to a reaction product of which the radical R represents an etherified lower hydroxyalkyl group.

Etherification can be performed by reaction of the hydroxyalkyl compound, preferably in a solvent, in the presence of a condensation agent, with a reactive ester of an alcohol. Suitable reactive esters are, for example, ester of hydrohalic acids, e.g. hydrobromic acid or hydriodic acid, or sulphonic acid esters, e.g. o- or p-toluenesulphonic acid ester. As condensation agent, it is possible to use, for example, alkali alkanolates, e.g. sodium methylate or sodium ethylate, or alkali metal hydrides, e.g. sodium hydride, or metal amides such as sodium amide or lithium amide. Suitable solvents are inert solvent, e.g. hydrocarbons such as benzene or toluene, or, where alkanolates are used as condensation agents, corresponding alkanols. The reaction temperatures are preferably between 20° and 130° C.

A further possibility is where optionally a resultant product of the general formula I of which the radical R denotes an etherified lower hydroxyalkyl group is split to give a product of which the radical R represents a free lower hydroxyalkyl group.

The splitting of such an ether, especially of a compound of which the radical R is, for example, a monoarylmethoxy-lower-alkyl group or diarylmethoxy-lower-alkyl group, is preferably performed with the aid of hydrohalic acids such as hydrochloric acid, hydriodic acid or, in particular, hydrobromic acid. It is advantageous to use the hydrohalic acids in a solvent. Suitable solvents are, e.g., carboxylic acids such as acetic acid. The reaction temperature is about 20° to 150° C. The splitting of a 2-oxocycloalkoxy group, such as, e.g., the tetrahydropyran-2-yloxy-lower-alkyl group, is performed, e.g., likewise by the action of acids, such as, e.g., hydrohalic acids, in most cases, however, under milder conditions. For example, splitting is effected by the action of dilute aqueous hydrochloric acid, to which is added a water-miscible organic solvent, such as, e.g., methanol, at a temperature of approx. 50° to 100° C, or at the boiling temperature of the reaction mixture.

In another case, a resultant product of the general formula I of which the radical R denotes an acylated lower hydroxyalkyl group is optionally hydrolysed to a product of which the radical R represents a free lower hydroxyalkyl group.

Hydrolysis can be carried out in an alkaline or acid medium, preferably in a solvent, at a reaction temperature of about 20° to 150° C. The employed base is for example an alkali hydroxide, such as sodium or potassium hydroxide, which is preferably used in a solvent containing hydroxyl groups, e.g. in methanol or ethanol. The acid used is preferably a strong mineral acid, e.g. concentrated hydrochloric acid.

A further example is where a resultant product of the general formula I of which the radical R denotes a lower oxoalkyl group is reduced to a product of which the radical R represents a lower hydroxyalkyl group. The reduction of the oxyalkyl compounds can be performed by means of a complex metal hydride at a reaction temperature of about 20° to 70° C. There is used, in particular, lithium aluminium hydride, preferably in a solvent. Solvents that are especially suitable are ethereal liquids, e.g. ethers, tetrahydrofuran, dioxane, dibutyl ether, diisopropyl ether, butyl ethyl ether, diethylene glycoldiethyl ether or N-methylmorpholine.

According to a second variant of the process, the oxoalkyl compounds can be reduced with a metal alcoholate in the appropriate alkanol, or in a hydrocarbon such as, e.g. toluene or xylene, optionally under nitrogen. A particularly suitable reducing agent is aluminium isopropylate. A reaction temperature of about 20° to 145° C is maintained during the reaction.

Furthermore, a resultant product of the general formula I of which the radical R denotes an esterified lower carboxyalkyl group can optionally be reduced to a product of which the radical R represents a free lower hydroxyalkyl group. This reduction can be performed by means of a complex hydride in an ethereal solvent. As complex hydride there is used, e.g., lithium aluminium hydride, and as ethereal solvent, e.g., tetrahydrofuran or ether. The reduction is preferably performed at a reaction temperature of between 20° and 70° C.

The invention relates also to those modifications of the process whereby a compound occurring as an intermediate at some stage is used as the starting material and the uncompleted steps are performed, or whereby the process is interrupted at some stage, or whereby a starting material is formed under the reaction conditions, or whereby a reaction constituent is optionally present in the form of its salts.

Depending on the choice of starting materials and working procedures, the new compounds can be present as optical antipodes or as racemates or, provided that they have at least two asymmetric carbon atoms, also as racemate mixtures and/or as pure geometric isomers or as mixtures thereof (isomer mixtures).

Mixtures of isomers obtained can, by virtue of the physicochemical differences in the constituents, be separated on a known manner, into the two pure geometric isomers; e.g. by chromatography on a suitable stationary phase, such as with a complex-forming heavy-metal compound, e.g. with a silver compound, with a pretreated silica gel or aluminium oxide, or by formation of a heavy-metal addition compound, e.g. of the silver nitrate complex, separation thereof into the addition compounds of the pure isomers, e.g. by fractional crystallisation, and subsequent liberation of the pure isomers.

Pure isomers obtained, e.g. trans isomers, can be converted in the usual manner, e.g. photochemically, for example by irradiation with light of suitable wavelength, advantageously in a suitable solvent such as in an aliphatic hydrocarbon, or in the presence of a suitable catalyst, into the respective oppositely configurated isomers, e.g. into the cis isomers.

By virtue of the physicochemical differences in the constituents, racemate mixtures can be separated in a known manner into the two stereoisomeric (diastereomeric) pure racemates, for example by chromatography and/or fractional crystallisation.

Resultant racemates can be resolved by known methods, e.g. by recrystallisation from an optically active solvent, with the aid of microorganisms, or by reaction with an optically active acid which forms salts with the racemic compound, and separation of the salts obtained in this manner, e.g. by virtue of their different degrees of solubility, into the diastereomeric salts, from which the antipodes can be liberated by the action of suitable agents. Particularly suitable optically active acids are, e.g., the D- and L-forms of tartaric acid, di-o-toluyltartaric acid, malic acid, mandelic acid, camphorsulphonic acid or quinic acid.

Depending on the conditions of the process and on the starting materials, the final materials are obtained in the free form, or in the form of their acid addition salts that are likewise embraced by the invention. There can thus be obtained, for example, basic, neutral or mixed salts, optionally also hemi-, mono-, sesqui- or polyhydrates thereof. The acid addition salts of the new compounds can be converted in a manner known per se into the free compounds, e.g. with basic agents such as alkalies or ion exchangers. Alternatively, the free bases obtained can form salts with organic or inorganic acids. For the production of acid addition salts there are used, in particular, such acids that are suitable for the formation of therapeutically usable salts. Examples of such acids are: hydrohalic acids, e.g. hydrochloric acid, acids of sulphur, e.g. sulphuric acid, acids of phosphorus, e.g. orthophosphoric acid, nitric acid, perchloric acid, aliphatic, alicyclic, aromatic or heterocyclic carboxylic or sulphonic acids, such as formic, acetic, propionic, succinic, glycolic, lactic, malic, tartaric, citric, ascorbic, maleic, hydroxymaleic pyruvic, fumaric, benzoic, p-aminobenzoic, anthranilic, p-hydroxybenzoic, salicylic or p-aminosalicylic, embonic, methanesulphonic, ethanesulphonic, hydroxyethanesulphonic, ethylnesulphonic, halobenzenesulphonic, toluenesulphonic, naphthalenesulphonic or sulphanilic acid; or methionine, tryptophane, lysine or arginine.

The free compounds are converted into their salts, for example, as follows: the acid desired as salt component, or a solution thereof, is added to a compound of the general formula I in an organic solvent; for the reaction, there are preferably chosen organic solvents in which the formed salt is difficulty soluble, so that it can be separated by filtration. Such solvents are, e.g., methanol, acetone, methyl ethyl ketone, acetone/ethanol, methanol/ether or ethanol/ether.

Resultant salts of the new compounds, such as, e.g., the picrates, can also be used for purification of the free bases obtained: the free bases are converted into salts, these are separated, and the bases are liberated again from the salts.

The new compounds can be used as pharmaceutical active substances, e.g. in the form of pharmaceutical preparations containing the active substances, or their salts, in admixture with a pharmaceutical, organic or inorganic, solid or liquid carrier material suitable for enteral or parenteral administration. Suitable substances for the formation of these preparations are those which do not react with the new compounds, such as, e.g. water, gelatine, lacrose, starch, stearic acid, magnesium stearate, talcum, colloidal silicon dioxide, vegetable oils, benzyl alcohols, gum, polyalkylene glycols, vaseline, cholesterin and other known medicinal excipients. The pharmaceutical preparations can be in the form, e.g., of tablets, dragees, capsules or suppositories; or they can be in liquid form as solutions (e.g. as elixiers or syrup), suspensions or emulsions. They are optionally sterilised and/or contain auxiliaries such as preservatives, stabilizers, wetting or emulsifying agents, salts for regulation of the osmotic pressure, or buffers. They may also contain other therapeutically valuable substances.

The following examples further illustrate the production of the new compounds of the general formula I, as well as of starting materials not hitherto known; the given examples are however in no way intended to limit the scope of the invention. The temperature values are in degrees Centigrade.

EXAMPLE 1

13.4 g of 9,10-bis-bromomethyl-phenanthrene [see S. Hauptmann, Chem. Ber. 93, 2604 (1960)] is added within one hour, with stirring, to a solution of 37.5 g of methylamine in 225 ml of methanol, with the reaction temperature being maintained at 45°–50°. The reaction mixture is stirred for a further hour at 50°, and the solvent and excess methylamine are subsequently distilled off. 50 ml of water is added to the residue, and the formed suspension is extracted with ether. The ethereal solution is washed with water, dried over potassium carbonate and concentrated by evaporation. The residue is recrystallised from acetone to yield 2-methyl-2,3-dihydro-1H-dibenz[e,g]isoindole, m.p. 122 –123°.

5.7 g of pure base is dissolved in 30 ml of acetone and the solution is neutralised with 2.4 g of methanesulphonic acid, whereupon the methanesulphonate crystallises out: it melts at 230°–234° after recrystallisation from abs. ethanol.

EXAMPLE 2

The following final products are produced by a procedure analogous to that of Example 1:

a. from 13.4 g of 9,10-bis-bromomethyl-phenanthrene and 52 g of ethylamine in 225 ml of methanol: 2-ethyl-2,3-dihydro-1H-dibenz[e,g]isoindole, m.p. 118°–119° (from acetone); methanesulphonate m.p. 224°–227° (from abs. ethanol);

b. from 14.4 g of 9,10-bis-bromomethyl-phenanthrene and 71 g of isopropylamine in 150 ml of methanol: 2-isopropyl-2,3-dihydro-1H-dibenz[e,g]isoindole, m.p. 120°–121° (from petroleum ether); methanesulphonate m.p. 250°–255° (from abs. ethanol);

c. from 16.0 g of 9-chloromethyl-10-bromomethyl-phenanthrene and 23.5 g of 2-aminoethanol in 100 ml of methanol: 2-(2-hydroxyethyl)-2,3-dihydro-1H-dibenz[e,g]isoindole, m.p. 178°–180° (from ethanol); methanesulphonate m.p. 194°–196° (from abs. ethanol);

d. from 47 g of 9-chloromethyl-10-bromomethyl-phenanthrene and 84 g of allylamine in 300 ml of methanol: 2-allyl-2,3-dihydro-1H-dibenz[e,g]isoindole, m.p. 124°–125° (from acetone); methanesulphonate m.p. 190°–193° (from abs. ethanol);

e. from 16 g of 9-chloromethyl-10-bromomethyl-phenanthrene and 37.5 g of 3-aminopropanol in 100 ml of methanol: 2-(3-hydroxypropyl)-2,3-dihydro-1H-dibenz[e,g]isoindole, m.p. 175°–180° (crude product); methanesulphonate m.p. 194°–196° (from abs. ethanol);

f. from 16.0 g of 9-chloromethyl-10-bromomethyl-phenanthrene and 37.5 g of 2-methoxyethylamine in 100 ml of methanol: 2-(2-methoxyethyl)-2,3-dihydro-1H-dibenz[e,g]isoindole, m.p. 63°–64° (from pentane); methanesulphonate m.p. 190°–193° (from abs. ethanol).

EXAMPLE 3

250 g of 2-ethyl-2,3-dihydro-1H-dibenz[e,g]isoindole is mixed with 172.80 g of lactose and 169.70 g of potato starch; the mixture is moistened with an alcoholic solution of 10 g of stearic acid, and then granulated through a sieve. The granulate is then dried and there are subsequently added to 160 g of potato starch, 200 g of talcum, 2.50g of magnesium strearate and 32 g of colloidal silicon dioxide; the mixture is pressed to form 10,000 tablets each weighing 100 mg and each containing 25 mg of active substance: the tablets are optionally provided with grooves to give a more precise adjustment of the dosage amount.

EXAMPLE 4

A granulate is prepared from 250 g of 2-ethyl-2,3-dihydro-1H-dibenz[e,g]isoindole, 175.90 g of lactose and the alcoholic solution of 10 g of stearic acid; after drying, the granulate is mixed with 56.60 g of colloidal silicon dioxide, 165 g of talcum, 20 g of potato starch and 2.50 g of magnesium stearate, and the mixture is pressed to form 10,000 dragee cores. These are subsequently coated with a concentrated syrup made from 502.28 of cryst. saccharose, 6 g of shellac, 10 g of gum arabic, 0.22 g of dyestuff and 1.5 g of titanium dioxide, and then dried. The dragees obtained each weigh 120 mg and each contain 25 mg of active substance.

EXAMPLE 5

In order to produce 1000 capsules each containing 25 mg of active substance, 25 g of 2-ethyl-2,3-dihydro-1H-dibenz[e,g]isoindole is mixed with 248.0 g of lactose; the mixture is uniformly moistened with an aqueous solution of 2.0 g of gelatine, and is put through a suitable sieve (e.g. Sieve III according to Ph.Helv. V). The granulate is mixed with 10.0 g of dried maize starch and 15.0 g of talcum, and the mixture is evenly filled into 1000 hard gelatine capsules, Size 1.

EXAMPLE 6

A suppository mixture is prepared from 2.5 g of 2-ethyl-2,3-dihydro-1H-dibenz[e,g]isoindole and 167.5 g of adeps solidus, and the mixture is used to pour 100 suppositories each containing 25 mg of active substance.

EXAMPLE 7

A solution of 25 g of 2-ethyl-2,3-dihydro-1H-dibenz[e,g]isoindole-methanesulphonate in one liter of water is filled into 1000 ampoules, and then sterilised. An ampoule contains a 2.5% solution of 25 mg of active substance.

EXAMPLE 8

By procedures analogous to those of Examples 3 to 8, it is possible to produce tablets, dragees, capsules, suppositories and ampoules also from the following compounds and from their salts:
2-methyl-2,3-dihydro-1H-dibenz[e,g]isoindole,
2-isopropyl-2,3-dihydro-1H-dibenz[e,g]isoindole,
2-allyl-2,3-dihydro-1H-dibenz[e,g]isoindole,
2,3-dihydro-1H-dibenz[e,g]isoindole-2-ethanol,
2,3-dihydro-1H-bibenz[e,g]isoindole-2-propanol,
2-(2-methoxyethyl)-2,3-dihydro-1H-dibenz[e,g-]isoindole.

What is claimed is:

1. A 2,3-Dihydro-1H-dibenz[e,g]isoindole derivative selected from a compound of the formula I

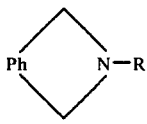

(I)

wherein
Ph represents the 9,10-phenanthrylene radical, and
R represents a lower alkyl, lower alkenyl, lower haloalkyl, lower hydroxyalkyl, lower-alkoxy-lower-alkyl, lower-alkanoyloxy-lower alkyl, lower oxoalkyl, lower carboxy-alkyl or lower-alkoxycarbonyl-lower-alkyl group
and the pharmaceutically acceptable salts thereof with inorganic and organic acids.

2. A compound according to claim 1 wherein Ph represents the 9,10-phenanthrylene radical, and R represents a lower alkyl group having 1 to 6 carbon atoms, the allyl group, a lower hydroxyalkyl group having 2 to 6 carbon atoms, or a lower-alkoxy-lower-alkyl group having 3 to 6 atoms.

3. A compound according to claim 1 which is 2-Methyl-2,3-dihydro-1H-dibenz[e,g]isoindole or a pharmaceutically acceptable salt thereof.

4. The methanesulphonic acid salt of the compound of claim 3.

5. 2-Ethyl-2,3-dihydro-1H-dibenz[e,g]isoindole or a pharmaceutically acceptable salt thereof.

6. The methanesulphonic acid salt of the compound of claim 5.

7. 2-Isopropyl-2,3-dihydro-1H-dibenz[e,g]isoindole or a pharmaceutically acceptable salt thereof.

8. The methanesulphonic acid salt of the compound of claim 7.

9. 2-Allyl-2,3-dihydro-1H-dibenz[e,g]isoindole or a pharmaceutically acceptable salt thereof.

10. The methanesulphonic acid salt of the compound of claim 9.

11. 2-(2-Hydroxyethyl)-2,3-dihydro-1H-dibenz[e,g-]isoindole or a pharmaceutically acceptable salt thereof.

12. The methanesulphonic acid salt of the compound of claim 11.

13. 2-(3-Hydroxypropyl)-2,3-dihydro-1H-dibenz[e,g]isoindole or a pharmaceutically acceptable salt thereof.

14. The methanesulphonic acid salt of the compound of claim 13.

15. 2-(2-Methoxyethyl)-2,3-dihydro-1H-dibenz[e,g-]isoindole or a pharmaceutically acceptable salt thereof.

16. The methanesulphonic acid salt of the compound of claim 15.

17. Pharmaceutical preparations containing a compound of the formula I according to claim 1 or a pharmaceutically acceptable salt of such a compound, together with a pharmaceutically acceptable carrier material.

18. Pharmaceutical preparations according to claim 17 containing 2-ethyl-2,3-dihydro-1H-dibenz[e,g-]isoindole or the methanesulfonic acid salt thereof.

19. The method of producing an antidepressive effect in a warm-blooded animal which comprises administering to said warm-blooded animal an antidepressive effective amount of a compound of the formula I according to claim 1 or one of its pharmaceutically acceptable salts.

* * * * *